United States Patent
Huang et al.

(10) Patent No.: US 8,934,010 B2
(45) Date of Patent: Jan. 13, 2015

(54) METHOD FOR SMEAR MEASUREMENT OF DISPLAY DEVICE AND DEVICE FOR SMEAR MEASUREMENT OF DISPLAY DEVICE

(75) Inventors: Guochuan Huang, Shenzhen (CN); Hao Jin, Shenzhen (CN); Jianli Dai, Shenzhen (CN)

(73) Assignee: Shenzhen China Star Optoelectronics Technology Co., Ltd., Shenzhen (CN)

( * ) Notice: Subject to any disclaimer, the term of this patent is extended or adjusted under 35 U.S.C. 154(b) by 675 days.

(21) Appl. No.: 13/378,088

(22) PCT Filed: Dec. 9, 2011

(86) PCT No.: PCT/CN2011/083736
§ 371 (c)(1),
(2), (4) Date: Dec. 14, 2011

(87) PCT Pub. No.: WO2013/075371
PCT Pub. Date: May 30, 2013

(65) Prior Publication Data
US 2013/0128033 A1     May 23, 2013

(30) Foreign Application Priority Data
Nov. 21, 2011 (CN) .......................... 2011 1 0371598

(51) Int. Cl.
*H04N 7/18*     (2006.01)
*H04N 17/04*    (2006.01)
(Continued)

(52) U.S. Cl.
CPC ............... *H04N 17/04* (2013.01); *H04N 7/181* (2013.01); *G01C 15/00* (2013.01); *G01B 11/022* (2013.01); *H04N 7/18* (2013.01); *G01N 11/00* (2013.01)
USPC .......................................... 348/135; 382/107

(58) Field of Classification Search
CPC ...... G01B 11/022; G01B 11/024; H04N 7/18; H04N 7/181; G01C 15/00
USPC ........................................................... 348/135
See application file for complete search history.

(56) References Cited

U.S. PATENT DOCUMENTS 5,771,406 A * 6/1998 Sakamoto et al. .............. 396/55
6,211,854 B1 * 4/2001 Fujiyoshi ......................... 345/10
(Continued)

FOREIGN PATENT DOCUMENTS

CN      1450513 A    10/2003
CN    101425246 A     5/2009
(Continued)

OTHER PUBLICATIONS

Luo Bin, The International Searching Authority written comments, Jun. 2012, CN.
(Continued)

*Primary Examiner* — Geepy Pe
*Assistant Examiner* — Howard D Brown, Jr.
(74) *Attorney, Agent, or Firm* — IPro, Inc.; Na Xu

(57) ABSTRACT

The present invention discloses a method for smear measurement of display device and a device for smear measurement of display device which comprises the following steps: a flash with a moving pattern and an unmovable scale is played in the display device; the smear extent of the moving pattern is judged in accordance with the scale number occupied by the smear in the flash. The present invention plays a flash with a moving pattern and an unmovable scale in the display device and judges smear extent of the moving pattern in accordance with the scale number occupied by the smear in the flash, so that the smear can be quantified by scales and different scale numbers corresponding to different smear extents are formed, to accurately judge the smear extent by observing the scale number occupied by the smear, thereby effectively monitoring the product quality.

16 Claims, 3 Drawing Sheets

(51) Int. Cl.
*G06K 9/00* (2006.01)
*G01C 15/00* (2006.01)
*G01B 11/02* (2006.01)
*G01N 11/00* (2006.01)

(56) References Cited

U.S. PATENT DOCUMENTS

| | | | |
|---|---|---|---|
| 6,859,192 B1* | 2/2005 | Ogawa | 345/77 |
| 7,133,070 B2* | 11/2006 | Wheeler et al. | 348/223.1 |
| 7,330,569 B2* | 2/2008 | Lin | 382/107 |
| 7,499,584 B2* | 3/2009 | Delaney | 382/152 |
| 8,040,407 B2* | 10/2011 | Hirai | 348/248 |
| 2011/0169795 A1* | 7/2011 | Kondoh et al. | 345/207 |
| 2011/0304893 A1* | 12/2011 | Sakai | 358/513 |
| 2013/0100282 A1* | 4/2013 | Siercks | 348/135 |

FOREIGN PATENT DOCUMENTS

| | | |
|---|---|---|
| CN | 101425246 A | 5/2009 |
| CN | 101478692 A | 7/2009 |
| CN | 101478692 A | 7/2009 |
| CN | 101762921 A | 6/2010 |
| JP | 2010-91711 A | 4/2010 |

OTHER PUBLICATIONS

Liu Duoduo, The first office action, Jun. 2013, CN.

* cited by examiner

METHOD FOR SMEAR MEASUREMENT OF DISPLAY DEVICE AND DEVICE FOR SMEAR MEASUREMENT OF DISPLAY DEVICE

TECHNICAL FIELD

The present invention relates to the field of liquid crystal display (LCD), and more particularly to a method for smear measurement of LCD module and a device for smear measurement of display device.

BACKGROUND

With the continuous development of TFT LCD (Thin Film Transistor Liquid Crystal Display) technology, the TFT LCD has become an important display platform of modern IT and video products. The TFT-LCD controls the arrangement form of liquid crystal molecules through the electromagnetic field between an array glass substrate and a CF (Colour Film) glass substrate, so that the light through the liquid crystal deflects to form different penetration rates, thereby achieving the display principle. The certain time required for the liquid crystal molecules to turn from the deflection state to the normal state and then to the deflection state is called response time. The smear caused by the over-long response time of the crystal has become an important factor that affects quality of the TFT-LCD.

Smear refers to the phenomenon that the moving object leaves a residual image on the background or that the background leaves a residual image on the moving object, when the image of an object moving relative to a static background is displayed. The smear includes the bright smear and the black smear which include the point smear and the line smear. In addition, the smear includes the vertical smear and the horizontal smear from the point of direction. FIG. 1 and FIG. 2 respectively show display states of the bright smear and the black smear in the liquid crystal display. As shown in the figure, a black moving pattern 3 moves rapidly toward the left with a smear 4 behind. The smear 4 becomes the factor that affects the display quality, therefore how to accurately judge the smear extent has become an important basis for judging the quality of the display device.

The smear measurement at present mainly uses a simple flash to simulate forming of the smear and judges the smear severity through the comparison by visual observation. This method is unable to accurately and effectively judge the smear extent, therefore the display quality of the display device can not be accurately judged.

SUMMARY

One aim of the present invention is to provide a method for smear measurement of display device and a device for smear measurement of display device.

The aim of the present invention is achieved by the following technical schemes: a method for smear measurement of display device comprises the following steps:

A: A flash with a moving pattern and an unmovable scale is played in the display device.

B: The smear extent of the moving pattern is judged in accordance with the scale number occupied by the smear in the flash.

Preferably, in step B, the picture displayed on the display device is firstly acquired by using an image acquisition device, wherein the picture comprises the scale, the moving pattern and the smear thereof; then the scale number of the smear on the image is read to judge the smear extent of the moving pattern. The picture displayed is acquired by the image acquisition device, to obtain a static picture. The smear extent can be accurately judged by judging the scale number occupied by the smear of the moving pattern on the acquired picture.

Preferably, the flash picture has multiple moving patterns with different moving speeds and scales for measuring smears of the different moving patterns.

Preferably, the scale comprises: type marks corresponding to different moving speeds and scales corresponding to type marks. The flash picture has eight scales for measuring smears of the pictures with different moving speeds. The smear state of the display device is comprehensively judged through smear extents of patterns with various moving speeds.

Preferably, the flash comprises one or more pictures for measuring: bright smear or black smear or point smear or line smear or vertical smear or horizontal smear.

Preferably, multiple flashes are used to measure display devices of different sizes and resolutions. Corresponding flashes are selected in accordance with sizes and resolutions of display devices prior to step A. Corresponding flashes are selected in accordance with display devices of different sizes and resolutions, so that the smear extents of display devices can be accurately measured.

Preferably, in step B, the image acquisition device is a digital camera with high photosensitive speed. The picture acquired by the digital camera with high photosensitive speed has a good quality, and can be stored in form of data.

Preferably, the flash is of flash form. The flash is easy to make and has a good picture quality.

Preferably, the display device is an LCD device.

A method for smear measurement of display device comprises the following steps:

α. A flash with a moving pattern is played in the display device.

β. The picture displayed on the display device is acquired by using the image acquisition device, and the smear of the acquired picture is measured with a scale tool.

Preferably, in step β, the scale tool is the digital image with scales. The scale number occupied by the smear is obtained by comparing the digital image with scales with the acquired picture, thereby achieving aims of quantifying smear and reading smear extent.

Preferably, in step β, the scale tool is an image analyzing software which has the database of smear states corresponding to the scale. The smear is measured to obtain the quantized value of the smear through analyzing the acquired picture by the image analyzing software. The quantized value of the smear extent can be rapidly and accurately obtained by the image analyzing software which has the database of smear states corresponding to the scale.

A device for smear measurement of display device, wherein the device comprises a flash player connected to the display device and an image acquisition device for acquiring flash pictures.

The present invention plays a flash with a moving pattern and an unmovable scale in the display device and judges smear extent of the moving pattern in accordance with the scale number occupied by the smear in the flash, so that the smear can be quantified by the scale and different scale numbers corresponding to different smear extents are formed, to accurately judge the smear extent by observing the scale number occupied by the smear, thereby effectively monitoring the product quality.

Wherein: 1. Type mark; 2. Scale; 3. Moving pattern; 4. Smear.

DETAILED DESCRIPTION

The present invention will further be described in detail in accordance with the figures and the preferred examples.

The method for smear measurement of display device of the present invention comprises the following steps: A: a flash with a moving pattern and an unmovable scale is played in the display device; B: the smear extent of the moving pattern is judged in accordance with the scale number occupied by the smear in the flash. The present invention plays a flash with a moving pattern and an unmovable scale in the display device and judges smear extent of the moving pattern in accordance with the scale number occupied by the smear in the flash, so that the smear can be quantified by the scale and different scale numbers corresponding to different smear extents are formed, to accurately judge the smear extent by observing the scale number occupied by the smear, thereby effectively monitoring the product quality.

There is also other scheme in the idea of the present invention which comprises the following steps: α. a flash with a moving pattern is played in the display device; β. the picture displayed on the display device is acquired by an image acquisition device, to measure the smear of the acquired picture with a scale tool. The scheme lies in that the scale does not exist in the flash picture but is additionally arranged. The scale can exist in multiple forms like a digital image and an image analysis software with database of the smear corresponding to the scale.

The major technical scheme of the present invention is discussed through several preferred examples as follows. In the example of the present invention, the flash used is of the flash form which is convenient to make.

Figure 1:
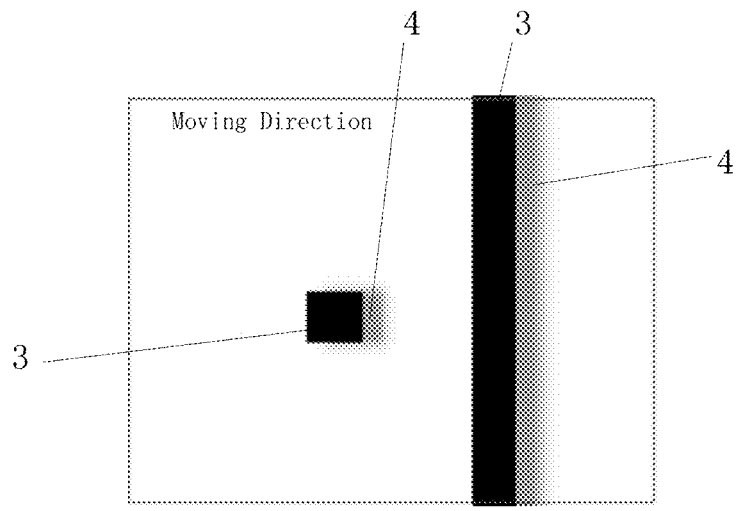
FIG. 1 is a schematic diagram of a bright smear of a liquid crystal display.
Figure 2:
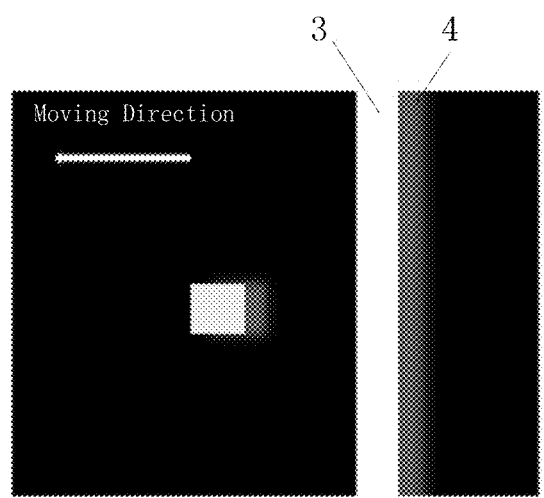
FIG. 2 is a schematic diagram of a black smear of a liquid crystal display.
Figure 3:
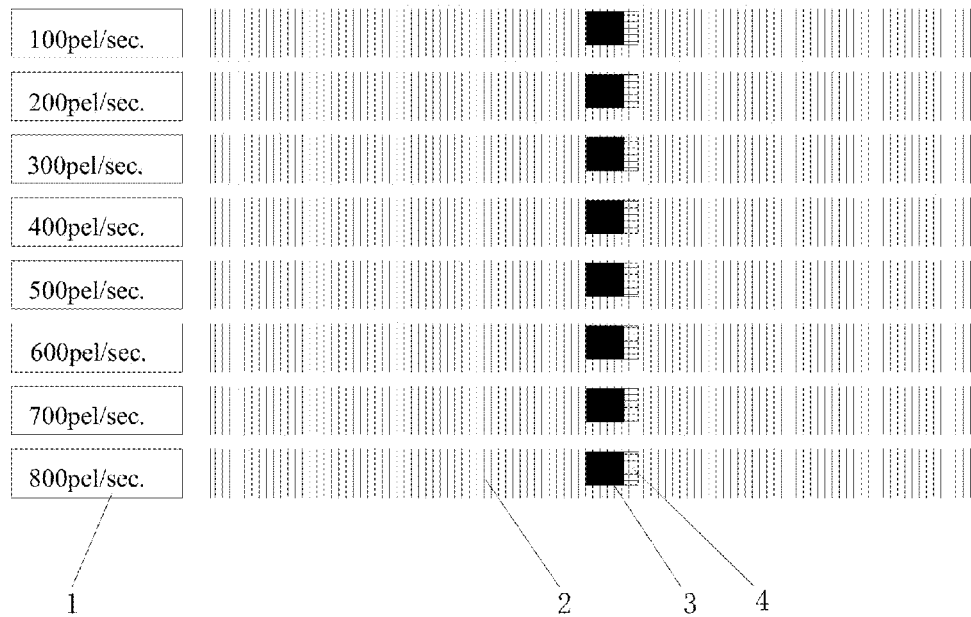
FIG. 3 is a first example of the present invention.

FIG. 3 shows an example of the present invention measuring the state of the point smear in the horizontal direction of a white picture of the LCD device. In accordance with the steps of the present invention, the flash film of the point smear measurement in the white picture direction is played in the LCD device, and then the moving smear picture is captured by the digital camera with high photosensitive speed. FIG. 3 shows a smear picture captured by the digital camera with high photosensitive speed, wherein, the left are type marks 1 which respectively mark corresponding values of various moving speeds. There are scales 2 respectively corresponding to different speeds, and each row of scales correspond to a speed value. A black moving pattern 3 moves on each row of scales toward left at the speeds marked by type marks 1, and a smear 4 follows the moving pattern 3. As shown in the picture, the smear 4 is remained in the moving direction of the moving pattern 3. Taking the width of smear 4 of the moving pattern 3 corresponding to the scale speed of 800 pel/sec. in the bottom row and the scale as example, the smear 4 occupies three scales 2, that is, the extent of the smear 4 at the moving speed of 800 pel/sec. can be quantified and represented by the three scales, and the smear value is 3. The picture of the flash film comprises total eight rows of scales 2 corresponding to different moving speeds. Each row of scales 2 correspond to a moving pattern 3 which is moving at the moving speed marked on the row, thereby simultaneously measuring, in a picture, the smear 4 extents of eight moving patterns with different moving speeds.

Figure 4:
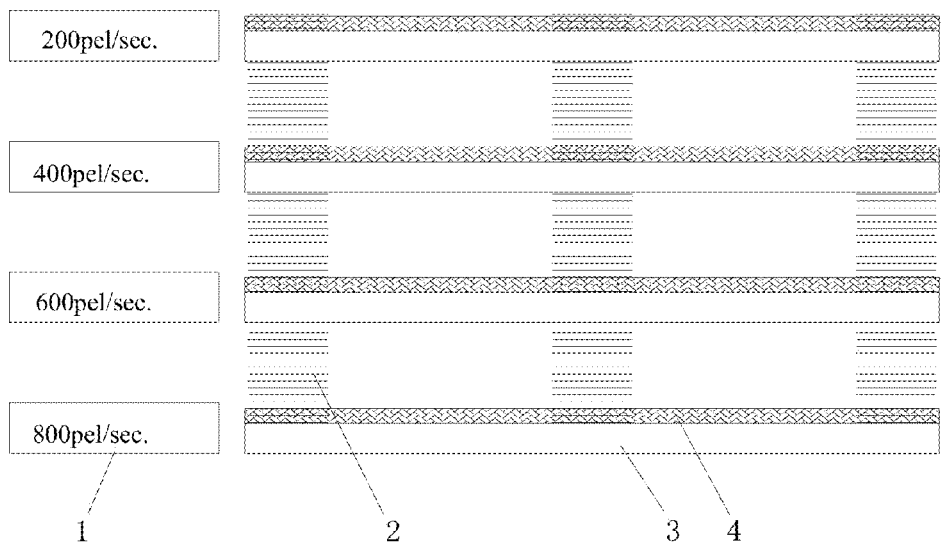
FIG. 4 is a second example of the present invention.
Figure 5:
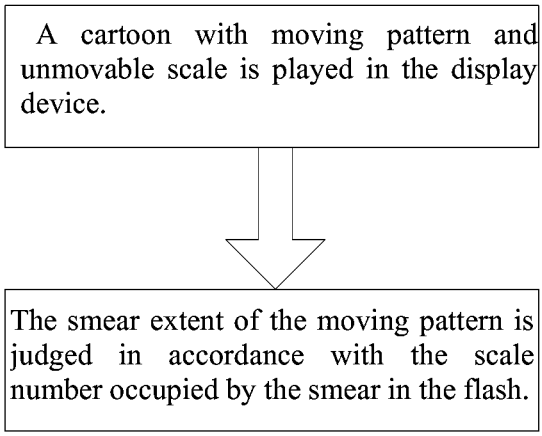
FIG. 5 is a flow diagram of a scheme of the present invention.

As shown in FIG. 4, a second example of the present invention is different from the first example in that the second example measures the vertical smear by using a black picture (the background in the figures does not show the black). The flash film corresponds to the vertical smear measurement film of the black picture, and the figure shows a flash film picture which is captured by a camera with high photosensitive speed. In the picture, scales 2 are horizontally arranged and comprise total three rows of scales 2. In the example, only one row of scales 2 can also be used. All the same, the smear extent is judged by analyzing and reading the scale 2 number occupied by the smear 4. The moving pattern 3 moves at the marked speed when moving to corresponding speed marks, therefore, the flash film in the example can measure line smear extents of four different speeds.

Above are two examples of the present invention for measuring the smear extents of two moving pictures with different moving speeds. In addition to the two examples, the present invention can also make different flash measurement films, for example, display devices of different sizes and resolutions may require flashes of different sizes and resolutions, and flashes corresponding to various smears, for example, one or more pictures of bright smear or black smear, point smear or line smear or vertical smear or horizontal smear, in accordance with different requirements, thereby accurately and effectively measuring the smear extent of display devices.

Of course, prior to flash playing when measuring the smear, the size and resolution of the display device are firstly decided, and then corresponding flash is selected. Multiple smear flashes of the same display device can be played to record multiple smear extents, thereby comprehensively assessing display quality of the display device.

In addition, in the idea of the present invention, the manner of quantifying the smear can also use an outer scale like a digital image or an image analyzing software which has the database of the scale number corresponding to various smear extents. The picture acquired by the image acquisition device is transmitted into the image analyzing software and is analyzed to rapidly and accurately transmit out the smear extent, thereby effectively judging display quality of the display device.

In the two examples of the present invention, the scale is used to quantify the smear, so that the smear extent can be accurately read; and there is moving patterns with various moving speeds so that the smear extents of moving patterns with different moving speeds can be measured. In addition, corresponding flashes are made in accordance with various display devices of different sizes and resolutions, so that the measurement is more pertinent and accurate. Furthermore, the bright smear is distinguished from the black smear, the point smear is distinguished from the line smear, and the horizontal smear is distinguished from the vertical smear, to measure independently. For devices of different sizes and resolutions, the display quality of a display device is comprehensively judged by above modes with measured various data.

The present invention is described in detail in accordance with the above contents with the specific preferred examples. However, this invention is not limited to the specific examples. For the ordinary technical personnel of the technical field of the present invention, on the premise of keeping the conception of the present invention, the technical personnel can also make simple deductions or replacements, and all of which should be considered to belong to the protection scope of the present invention.

The invention claimed is:

1. A method for smear measurement of display device comprises the following steps:
   A: A flash with a moving pattern and an unmovable scale is played in the display device;
   B: Smear extent of the moving pattern is judged in accordance with the scale number occupied by the smear in the flash;
   wherein in step B, a picture displayed on the display device is acquired by using an image acquisition device, wherein, said picture comprises a scale, a moving pattern and a smear thereof then the scale number occupied by the smear on the picture is read to judge the smear extent of said moving pattern;
   wherein said flash picture has multiple moving patterns with different moving speeds and scales for measuring smears of said different moving patterns;
   wherein said scale comprises: type marks corresponding to different moving speeds and scales corresponding to type marks, said flash picture has eight scales for measuring smears of the pictures with different moving speeds.

2. The method for smear measurement of display device of claim 1, wherein said flash comprises one or more pictures for measuring: bright smear or black smear, point smear or line smear or vertical smear or horizontal smear.

3. The method for smear measurement of display device of claim 2, wherein said flash is of flash form.

4. The method for smear measurement of display device of claim 2, wherein said display device is an LCD device.

5. The method for smear measurement of display device of claim 1, wherein multiple flashes are used to measure display devices of different sizes and resolutions, and prior to step A, corresponding flashes are selected in accordance with sizes and resolutions of the display devices.

6. The method for smear measurement of display device of claim 5, wherein said flash is of flash form.

7. The method for smear measurement of display device of claim 5, wherein said display device is an LCD device.

8. The method for smear measurement of display device of claim 1, wherein in step B, said image acquisition device is a digital camera with high photosensitive speed.

9. The method for smear measurement of display device of claim 8, wherein said flash is of flash form.

10. The method for smear measurement of display device of claim 8, wherein said display device is an LCD device.

11. The method for smear measurement of display device of claim 1, wherein said flash is of flash form.

12. The method for smear measurement of display device of claim 1, wherein said display device is an LCD device.

13. A method for smear measurement of display device comprises the following steps:
    A: A flash with a moving pattern and an unmovable scale is played in the display device;
    B: Smear extent of the moving pattern is judged in accordance with the scale number occupied by the smear in the flash;
    wherein in step B, a picture displayed on the display device is acquired by using an image acquisition device, wherein, said picture comprises a scale, a moving pattern and a smear thereof then the scale number occupied by the smear on the picture is read to judge the smear extent of said moving pattern;
    wherein said flash picture has multiple moving patterns with different moving speeds and scales for measuring smears of said different moving patterns;
    wherein said scale comprises: type marks corresponding to different moving speeds and scales corresponding to type marks, said flash picture has eight scales for measuring smears of the pictures with different moving speeds.

14. The method for smear measurement of display device of claim 13, wherein in step B, said scale tool is a digital image provided with scales.

15. The method for smear measurement of display device of claim 13, wherein in step B, said scale tool is an image analyzing software;
    said image analyzing software has the database of the smear states corresponding to said scale;
    said smear is measured to obtain the quantized value of the smear through analyzing aid acquired picture by said image analyzing software.

16. A device for smear measurement of display device, comprising: a flash player connected to said display device and an image acquisition device for acquiring flash pictures.

* * * * *